US008524490B2

(12) United States Patent
Lipscomb et al.

(10) Patent No.: US 8,524,490 B2
(45) Date of Patent: Sep. 3, 2013

(54) FULLY AUTOMATED PORTABLE DNA DETECTION SYSTEM

(75) Inventors: James H. Lipscomb, Kennett Square, PA (US); Richard Raffauf, Sr., Reading, PA (US); Richard Raffauf, Jr., legal representative, Reading, PA (US); Peter Blacklin, Columbia, MD (US); Michael Keating, Hardwick, NJ (US); Robert Bernstine, Chesapeake City, MD (US)

(73) Assignees: X-Bar Diagnostic Systems, Inc., Kennett Square, PA (US); James H. Lipscomb, Kennett Square, PA (US)

( * ) Notice: Subject to any disclaimer, the term of this patent is extended or adjusted under 35 U.S.C. 154(b) by 444 days.

(21) Appl. No.: 12/561,092

(22) Filed: Sep. 16, 2009

(65) Prior Publication Data

US 2010/0136632 A1 Jun. 3, 2010

Related U.S. Application Data

(60) Provisional application No. 61/098,161, filed on Sep. 18, 2008.

(51) Int. Cl.
*C12M 1/00* (2006.01)
*C12M 1/36* (2006.01)
*C12M 1/38* (2006.01)

(52) U.S. Cl.
USPC .................. 435/303.1; 435/286.2; 435/287.2; 435/287.3; 435/809

(58) Field of Classification Search
USPC .............. 435/303.1, 286.2, 287.2, 287.3, 809
See application file for complete search history.

(56) References Cited

U.S. PATENT DOCUMENTS

| | | | | |
|---|---|---|---|---|
| 3,878,357 | A * | 4/1975 | Marcoux | 219/209 |
| 4,683,195 | A | 7/1987 | Mullis et al. | |
| 4,683,202 | A | 7/1987 | Mullis | |
| 4,800,159 | A | 1/1989 | Mullis et al. | |
| 4,889,818 | A | 12/1989 | Gelfand et al. | |

(Continued)

FOREIGN PATENT DOCUMENTS

WO WO-2008/024080 A1 2/2008

OTHER PUBLICATIONS

Chien, Chao-Heng et al., "The Design and Fabrication of Platform Device for DNA Amplification," DTIP of MEMS & MOEMS, Apr. 26-28, 2006, XP-002578160, 7 pgs.

(Continued)

*Primary Examiner* — Nathan Bowers
*Assistant Examiner* — Gautam Prakash
(74) *Attorney, Agent, or Firm* — Foley and Lardner LLP

(57) ABSTRACT

Provided herein is a portable thermocycler, comprising: (i) a case; (ii) a rotary plate in the case; (iii) a plurality of heating blocks arranged in a geometric pattern disposed on the rotary plate; and (iv) at least one vessel adapted to move and contact at least two of the plurality of heating blocks; wherein each of the heating blocks comprises a heating plate maintained at a set temperature over a thermally insulating material; wherein the geometric pattern comprises a number of center heating blocks arranged in a shape defining a polygon and a number of outside heating blocks disposed around the periphery of the rotary plate; and wherein the rotary plate includes a plurality of rotating wheels adapted to rotate at least one of the vessels into contact with each of the heating blocks.

40 Claims, 12 Drawing Sheets

(56) References Cited

U.S. PATENT DOCUMENTS

| | | | | |
|---|---|---|---|---|
| 4,924,072 | A * | 5/1990 | Oslin | 219/401 |
| 4,965,188 | A | 10/1990 | Mullis et al. | |
| 5,023,171 | A | 6/1991 | Ho et al. | |
| 5,066,584 | A | 11/1991 | Gyllensten et al. | |
| 5,075,216 | A | 12/1991 | Innis et al. | |
| 5,079,352 | A | 1/1992 | Gelfand et al. | |
| 5,091,310 | A | 2/1992 | Innis | |
| 5,104,792 | A | 4/1992 | Silver et al. | |
| 5,719,378 | A * | 2/1998 | Jackson et al. | 219/497 |
| 6,303,343 | B1 * | 10/2001 | Kopf-Sill | 435/91.1 |
| 6,875,602 | B2 * | 4/2005 | Gutierrez | 435/286.2 |
| 7,081,226 | B1 * | 7/2006 | Wittwer et al. | 422/68.1 |
| 2004/0115799 | A1 | 6/2004 | Gutierrez | |
| 2004/0209331 | A1 | 10/2004 | Ririe | |
| 2007/0154922 | A1 | 7/2007 | Collier et al. | |
| 2007/0181703 | A1 * | 8/2007 | Buchanan et al. | 237/58 |
| 2008/0108119 | A1 * | 5/2008 | Jensen et al. | 435/173.1 |

OTHER PUBLICATIONS

Search Report and Written Opinion mailed May 7, 2010 in International Application No. PCT/US2009/057169.

McPherson et al. (1991) PCR 1: A Practical Approach (IRL Press at Oxford University Press).

Innis et al, PCR Protocols: A Guide to Methods and Applications, (Academic Press, New York, 1990.

* cited by examiner

System Block Diagram

(A) (B)

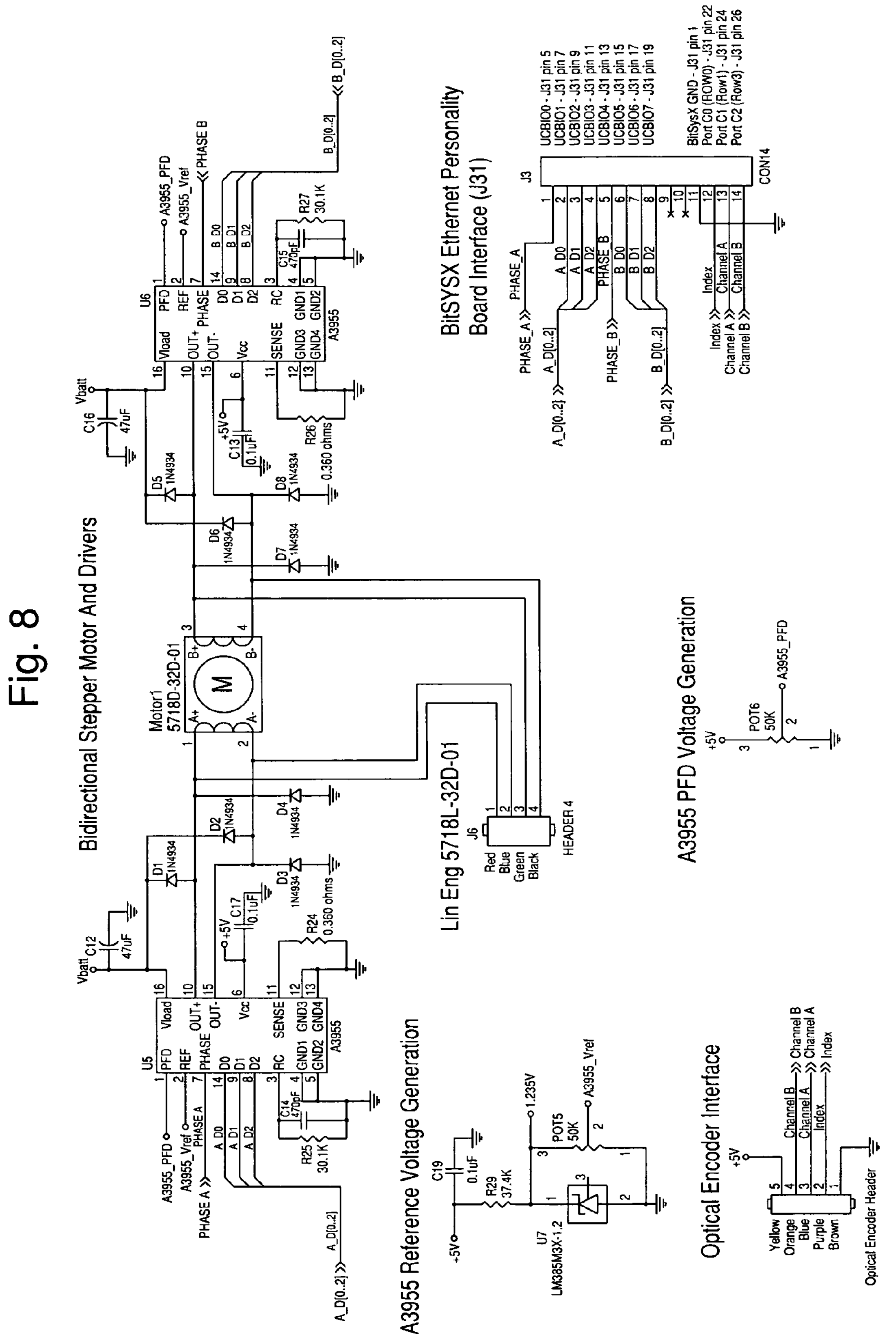
Fig. 8
Bidirectional Stepper Motor And Drivers
Motor1
5718D-32D-01
Lin Eng 5718L-32D-01
J6
HEADER 4
Red
Blue
Green
Black
BitSYSX Ethernet Personality
Board Interface (J31)
J3
CON14
UCBIO0 - J31 pin 5
UCBIO1 - J31 pin 7
UCBIO2 - J31 pin 9
UCBIO3 - J31 pin 11
UCBIO4 - J31 pin 13
UCBIO5 - J31 pin 15
UCBIO6 - J31 pin 17
UCBIO7 - J31 pin 19
BitSysX GND - J31 pin 1
Port C0 (ROW0) - J31 pin 22
Port C1 (Row1) - J31 pin 24
Port C2 (Row3) - J31 pin 26
U5
U6
A3955
R24 0.360 ohms
R26 0.360 ohms
R25 30.1K
R27 30.1K
C12 47uF
C16 47uF
C13 0.1uF
C17 0.1uF
C14 470pF
C15 470pF
1N4934
A3955 Reference Voltage Generation
U7
LM385M3X-1.2
R29 37.4K
C19 0.1uF
POT5 50K
A3955_Vref
A3955 PFD Voltage Generation
POT6 50K
A3955_PFD
Optical Encoder Interface
Optical Encoder Header
Yellow
Orange
Blue
Purple
Brown
Channel B
Channel A
Index Figure 11
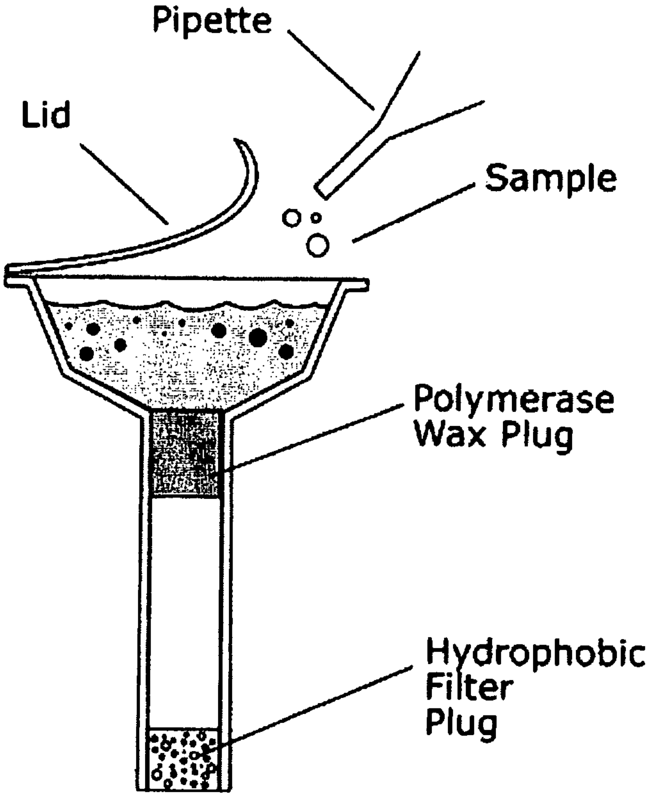
(A)
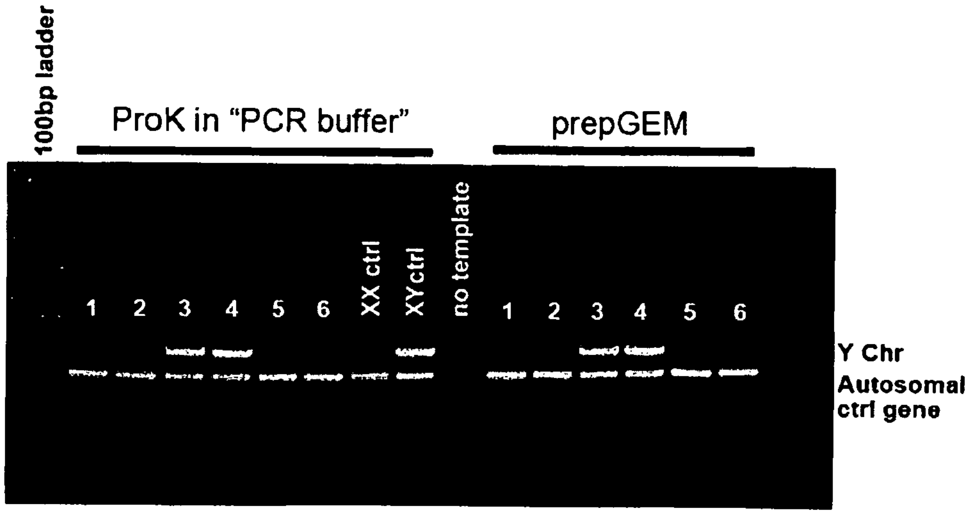
(B)

FULLY AUTOMATED PORTABLE DNA DETECTION SYSTEM

RELATED PATENT APPLICATIONS

This application claims priority from U.S. Provisional Application Ser. No. 61/098,161, filed Sep. 18, 2008, which is incorporated herein by reference in its entirety.

BACKGROUND OF THE INVENTION

Systems which utilize multiple or cyclic chemical reactions to produce a desired product often have careful temperature control to produce optimal results. Such reactions include nucleic acid amplification reactions such as the polymerase chain reaction (PCR) and the ligase chain reaction (LCR). However, because of the cost and difficulty associated with existing transportable testing equipment, such systems have thus far been unavailable in field-based operations.

A number of thermal "cyclers" used for DNA amplification and sequencing currently exist in the market, wherein the temperature controlled elements in these cyclers are heated and maintained at a certain desired temperature. However, these devices suffer drawbacks, such as high energy demand to operate, heat, and maintain the temperature at a prescribed level, and contamination, size and weight of the apparatus. These drawbacks often render the devices not practical in field operations.

Thus, there exists a need to develop a thermocycler system that is portable and can be operated without being connected to an external power source. It is further desirable to have such system with a long operating life and to be user-friendly, thereby adaptable for field use.

SUMMARY

It is an object of the present application to provide a portable thermocycler, and methods of making and using thereof. The thermocycler described herein can be deployed for field-use, where no power outlets are available.

One embodiment provides a heating block of a thermocycler, comprising: a heating plate mounted over a thermally insulating material having a thickness substantially greater than that of the heating plate, wherein the heating plate comprises a material having a thermal conductivity substantially higher than that of the thermally insulating material, and wherein the heating plate is maintained at a set temperature by a heater.

In another embodiment, a portable thermocycler is provided, the thermocycler comprising: (i) a case; (ii) a rotary plate in the case; (iii) a plurality of heating blocks arranged in a geometric pattern disposed on the rotary plate; and (iv) at least one vessel adapted to move and contact at least two of the plurality of heating blocks; wherein each of the heating blocks comprises a heating plate maintained at a set temperature mounted over a thermally insulating material; wherein the geometric pattern comprises a number of center heating blocks arranged in a shape defining a polygon and a number of outside heating blocks disposed around the periphery of the rotary plate; and wherein the rotary plate includes a plurality of rotating wheels adapted to rotate at least one of the vessels into contact with each of the heating blocks.

Another alternative embodiment provides a portable thermocycler, comprising: (i) a case; (ii) a rotary plate in the case; (iii) a plurality of heating blocks arranged in a geometric pattern disposed on the rotary plate; and (iv) at least one vessel adapted to move and contact at least two heating blocks; wherein at least some of the heating blocks comprise a heating plate maintained at a set temperature and mounted over a thermally insulating material having a thickness greater than that of the heating plate; wherein the temperature of the heating plates is controlled by a Proportional-Integral-Derivative (PID) heater; wherein the thermocycler is powered by at least one battery; and wherein the rotary plate includes a plurality of rotating wheels adapted to rotate at least one of the vessels into contact with the heating blocks.

In another embodiment, a portable thermocycler is provided, the thermocycler comprising: (i) a case; (ii) a rotary plate in the case; (iii) a plurality of heating blocks arranged in a geometric pattern disposed on the rotary plate; and (iv) at least one vessel adapted to move and contact at least two heating blocks; wherein each of the heating blocks comprises a heating plate maintained at a set temperature and mounted over a thermally insulating material having a thickness greater than that of the heating plate; wherein the thermocycler is powered by at least one battery; wherein the case comprises at least one photovoltaic cell and at least one display; and wherein the rotary plate includes a plurality of rotating wheels adapted to rotate at least one of the vessels into contact with each of the heating blocks.

In another embodiment, a portable thermocycler is provided, the thermocycler comprising: (i) a case; (ii) a rotary plate in the case; (iii) a plurality of heating blocks arranged in a geometric pattern disposed on the rotary plate; and (iv) at least one vessel adapted to move and contact at least two heating blocks; (v) a fluorescence detection system; wherein the heating blocks comprise a heating plate maintained at a set temperature and mounted over a thermally insulating material having a thickness greater than that of the heating plate; and wherein the rotary plate includes a plurality of rotating wheels adapted to rotate at least one of the vessels into contact with each of the heating blocks.

One embodiment provides a method of using a portable thermocycler, the method comprising: (i) powering a plurality of heating plates mounted over a plurality of thermally insulating materials; (ii) rotating at least one vessel adapted to contact at least two heating blocks, wherein the vessel carries a plurality of capillary tubes; and (iii) obtaining results by a fluorescence detection system, wherein the thermocycler is controlled by microprocessor, and wherein the thermocycler is powered by at least one battery.

One alternative embodiment provides a method of making a portable thermocycler comprising: (i) providing a plurality of heating plates mounted over a plurality of thermally insulating materials; (ii) providing a proportional-integral-derivative (PID) heater for each of the heating plates; (iii) providing a motor driven by a drive circuit to engage spider gears in the wheels; (iv) providing a fluorescence detection system; wherein the heating plates comprise a material having higher thermal conductivity than the thermally insulating materials; wherein the heating plates have a set temperature individually controlled by the PID heater and measured by a temperature measuring transducer; and wherein the motor is monitored by a position-identification device.

BRIEF DESCRIPTION OF THE DRAWINGS

FIG. 4A shows the assembly of the spider gears, and 4B shows the arrangement and assemblies of the cassettes and cassettes holders on the rotary plate.

FIG. 5A provides different views of the cassette; 5B illustrates different components of the cassette holder, and 5C illustrates the view of the cassette once assembled with the reaction vessels.

FIG. 8 shows a schematic of the circuit diagram of the motor, driver of the motor, and the encoder in one embodiment.

FIG. 10A provides an image of the thermocycler in a case; 10B shows a schematic of the design of the case, with a virtual keyboard and photovoltaic cells; 10C illustrates the foldable legs that can be expanded from the case to provide support to the case.

FIGS. 11A-11B provide exemplary results from a non-limiting working example. FIG. 11A shows a schematic of a sample solution containing a biological sample in the tube; 11B shows the results from a fluorescence reading after 20 cycles.

DETAILED DESCRIPTION

Figure 1:
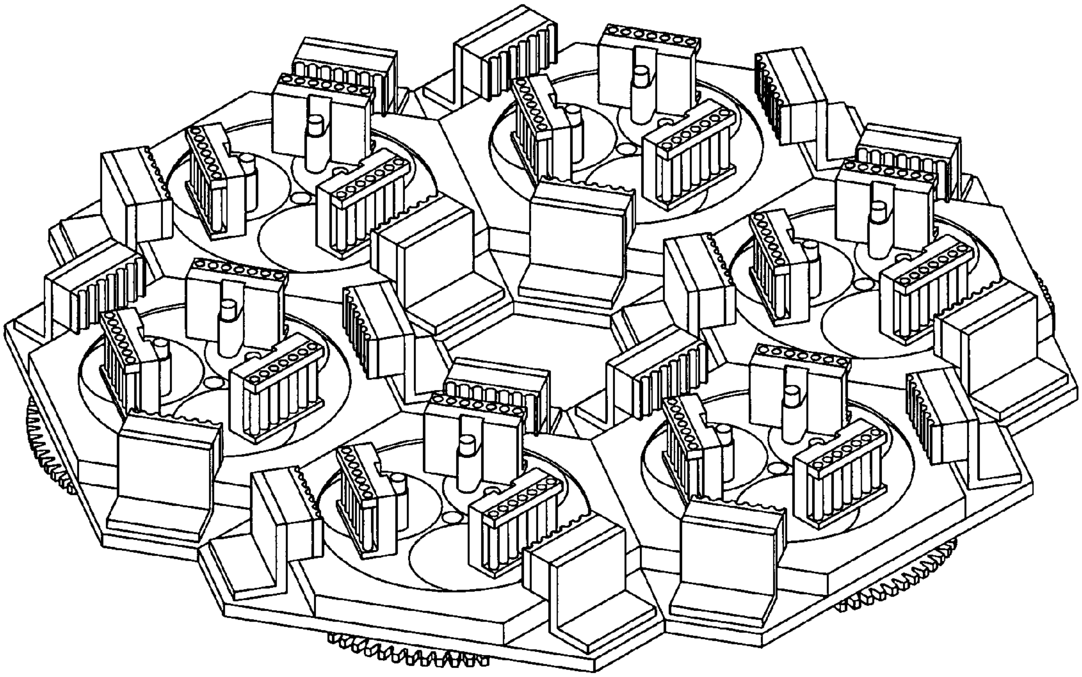
FIG. 1 provides a schematic of the overall design of the thermocycler.

All of the references cited herein are incorporated by reference in their entirety.

Introduction

Polymer chain reaction (PCR) is a technique involving multiple cycles that results in the geometric amplification of certain polynucleotide sequences each time a cycle is completed. The technique of PCR is well known in the art. The technique of PCR is described in many books, including, “PCR: A Practical Approach,” M. J. McPherson et al., IRL Press (1991), and “PCR Protocols: A Guide to Methods and Applications,” by Innis et al., Academic Press (1990). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584.

The PCR technique generally involves the step of denaturing a biomolecule, such as a polynucleotide, followed by heating (i.e., annealing) at least one pair of primer oligonucleotides to the denatured biomolecule, i.e., hybridizing the primer to the denatured biomolecule template. In the case of a polynucleotide, after annealing, an enzyme with polymerase activity can catalyze synthesis of a new polynucleotide strand that incorporates the primer oligonucleotide and uses the original denatured polynucleotide as a synthesis template. This series of steps—denaturation, primer annealing, and primer extension—constitutes a PCR cycle.

As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites can be amplified. The temperature of the reaction mixture is preferably varied during a PCR cycle, and consequently varied many times during a multicycle PCR experiment.

Several exemplary temperature cyclers can be found. For instance, the ROBOCYCLER thermocycler manufactured by Stratagene has four stations, but only one batch of samples is processed at a given time. The preferred operation for the ROBOCYCLER thermocycler appears to be for a single robot arm to move the single sample batch from station to station according to a pattern previously prescribed by a user. Another thermocycler design has been disclosed by U.S. Pat. No. 6,875,602 to Gutierrez. The thermocycler of Gutierrez comprises a plurality of heating blocks, each of which was heated to a prescribed temperature, and tri-pegged cams (or wheels). Because of the configuration and dimensions of certain parts of the thermocycler disclosed by Gutierrez, the device he describes would have a very high demand for energy during operation. Whether the device described is even operational is not established. Indeed, Gutierrez provides little if any details of key issues associated the operation of his device, failing to address the satisfaction of the high energy needs of his device altogether. Furthermore, the thermocycler of Gutierrez does not allow interfacing with an operator, thereby greatly diminishing its flexibility during field operation.

Overall Thermocycler Design

Figure 3A:
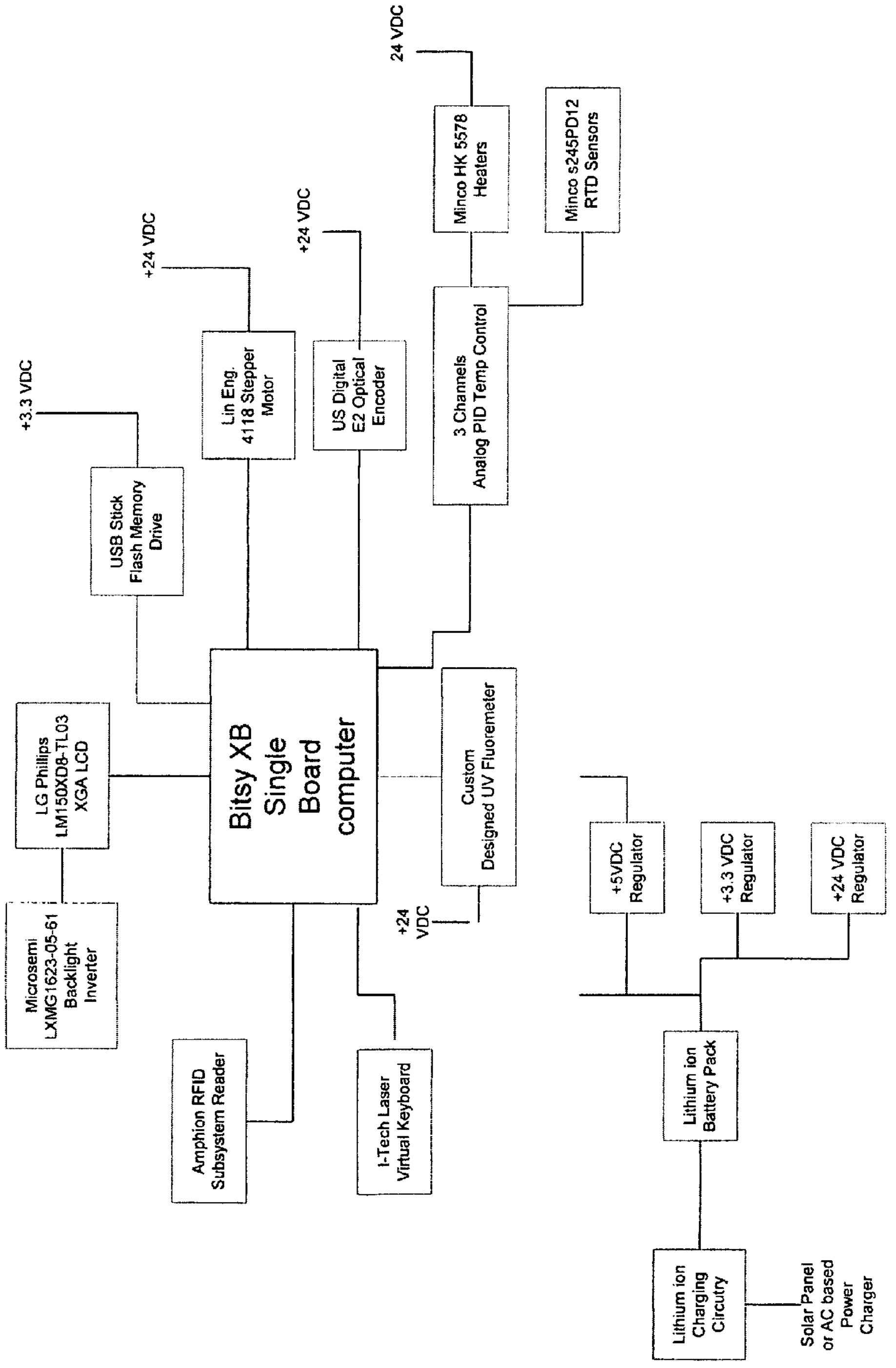
FIGS. 3A-3B provide schematics of the block diagrams of the system with all of its components and the circuit diagram of the heater system, respectively.

The thermocycler described herein can be employed as a field deployable thermocycler. It can be used for field-based operations, including in vitro diagnostics, insect testing, environmental testing, and water analysis. In most embodiments, the thermocycler comprises: (i) a case; (ii) a rotary plate in the case; (iii) a plurality of heating blocks arranged in a geometric pattern disposed on the rotary plate; and (iv) at least one vessel adapted to move and contact at least two of the plurality of heating blocks. At least some of the heating block comprise a heating plate that is maintained at a set temperature mounted over a thermally insulating material having a thickness greater than that of the heating plate. A schematic of the block diagram of a thermocycler in one embodiment is provided in FIG. 3A.

The heating block comprises a thin heating plate disposed over a thick thermally insulating material. The heating blocks can be arranged in various ways on the rotary plate. In one exemplary embodiment, a number of heating blocks in the middle of the rotary place (the “center” heating blocks) are arranged in a shape defining a polygon. The polygon can be of any shape, including a triangle, square, pentagon, or hexagon. The center heating blocks are surrounded by a number of heating blocks around the periphery of the rotating plate (the “outer” heating blocks”). The number of the outer heating blocks can vary. For example, it can be the same as the number of the faces of the polygon, or alternatively it can be at least twice as much as the number of the faces of the polygon; for example, twice, or thrice as much. In one embodiment, wherein the polygon is a hexagon as defined by the center heating blocks, twelve outer heating blocks are around the periphery of the rotary plate, as shown in FIG. 1.

Figure 2:
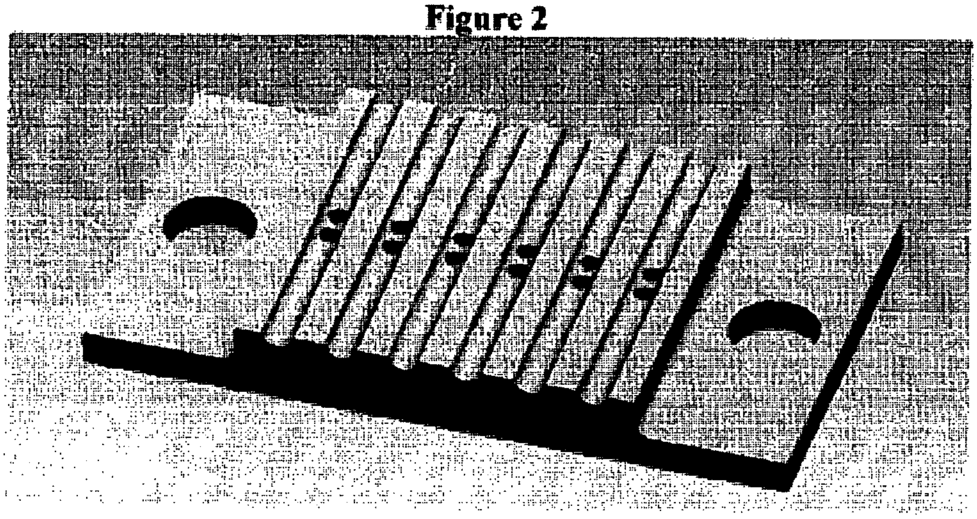
FIG. 2 shows a schematic of the design of the heating plate.
Figure 3B:
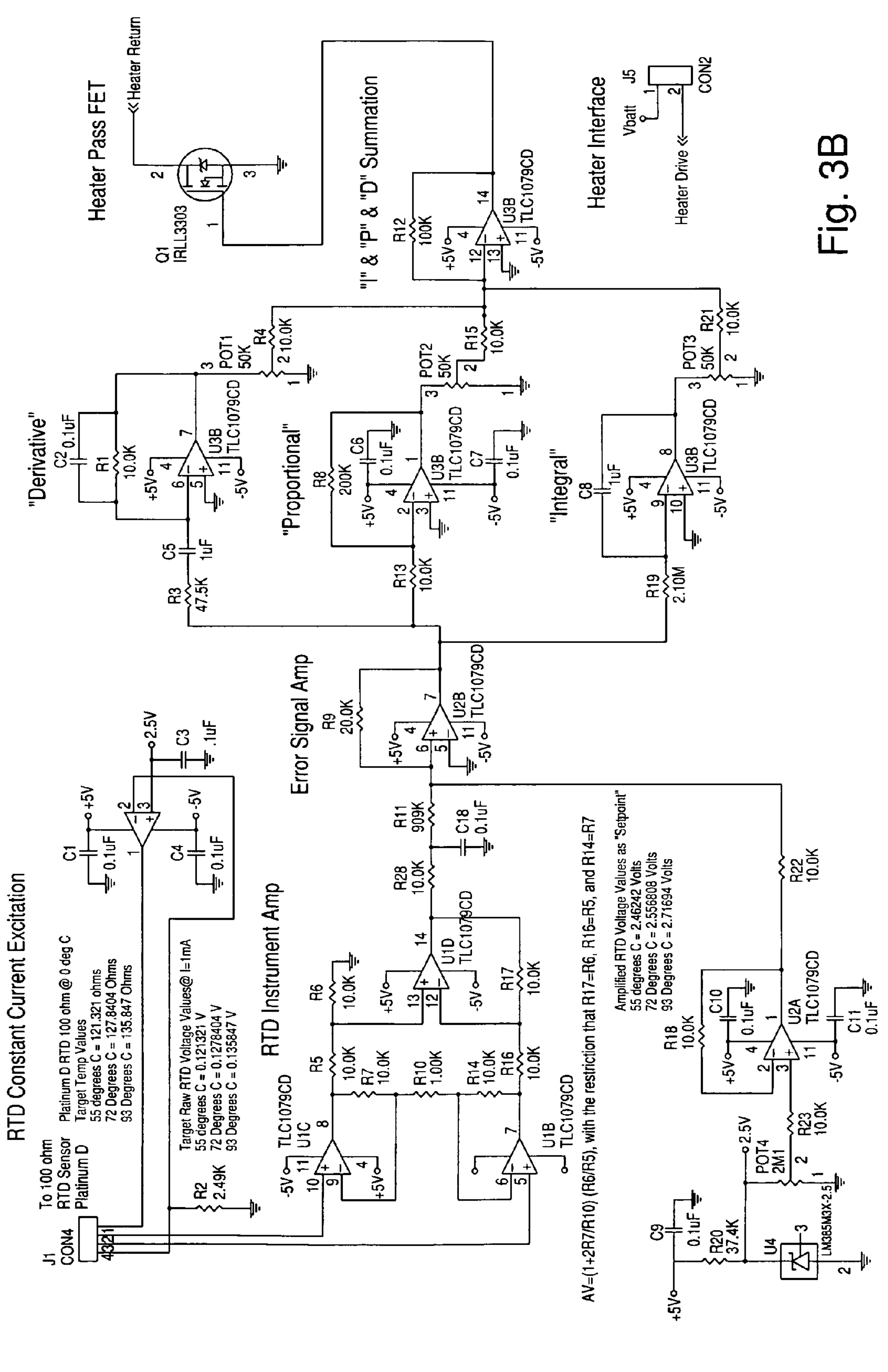

The heating plates over the heating blocks are preferably of a thin wall small thermal mass to allow quick heat transfer. The plates are preferably thinner than the thermally insulating material. The heating plates and blocks can be of any suitable size for a specific design. For example, the width of the heating plate can be between 0.5 inches and 2.5 inches, such as about 1.5 inch or less. The length of the heating plate can be between 0.25 inches and 2.5 inches, such as about 1.5 inch or less. The thickness of the heating plate can be between 0.1 inches and 1.5 inches, such as about 0.5 inch or less. In one embodiment, where 108 samples are tested in one setting, the heating plate has a width of about 0.89 inches, length of about 0.75 inches, and thickness of about 0.18 inches. The ratio of the thickness of the heating plate to that of the thermally insulating material can also vary. For example, it can be about less than about 1:20, about 1:10, about 1:5, or about 1.2, and preferably it is about 1:2. A schematic of the heating plate is provided in FIG. 2. The plates preferably comprises a material with a thermal conductivity that is substantially larger than that of the thermally insulating material. For example, the heating plate can comprise a metal, such as aluminum, whereas the thermally insulating material can comprise a heat insulator, including plastic such as thermoplastic, such as polyetherimide (e.g., ULTEM polyetherimide). The low thermal conductivity thermally insulating material can serve as large low conductivity masses to force heat transfer from the heater into the plate without absorbing the heat itself, thereby minimizing the electrical power waste. A schematic of the circuit diagram of the heating plates and the heater design connected to the plates is provided in FIG. 3B.

Figure 4:
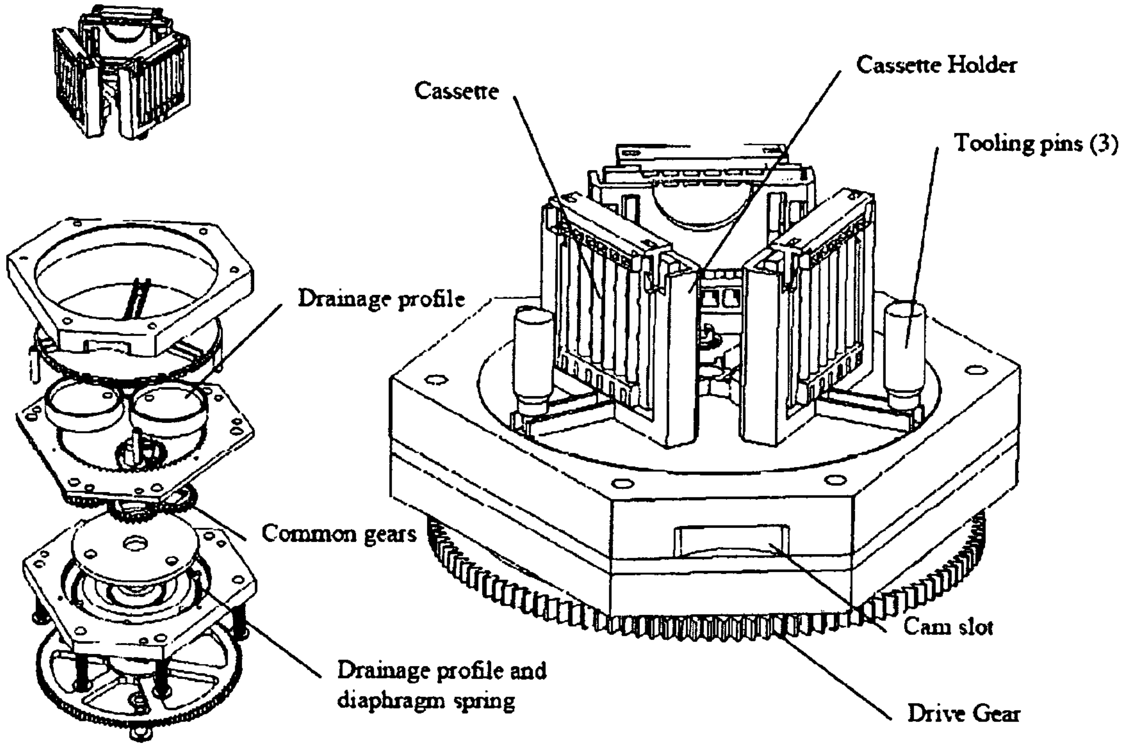
FIGS. 4A-4B provide an illustration of the components of the thermocycler, in particular the assembly of the gears, wheels, and the cassettes.
Figure 5A:
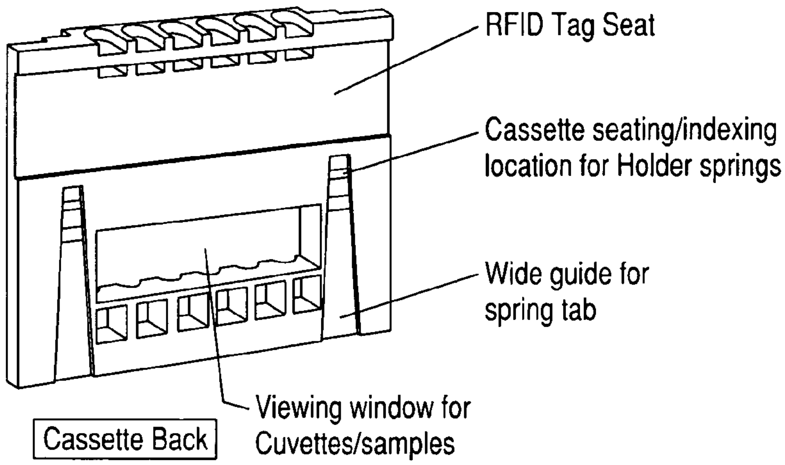
FIGS. 5A-5C provide schematics of the components and assembly of the cassettes.
Figure 5B:
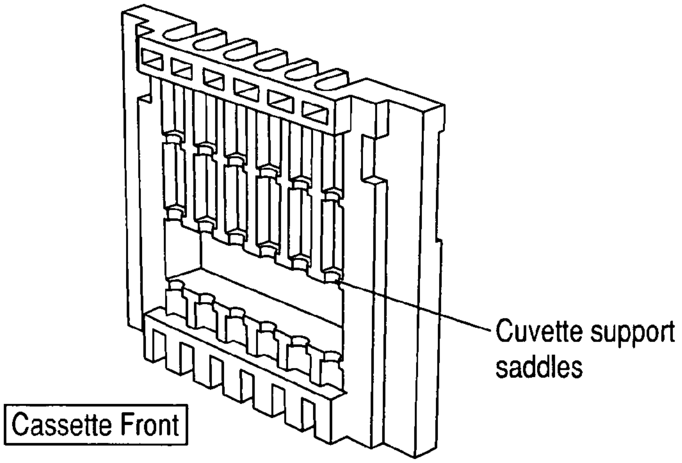
Figure 5C:
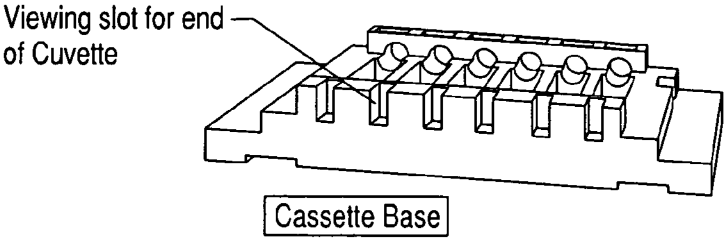

Also on the rotary plate can be a plurality of wheels. The wheels can be maneuvered by a plurality of gears, as shown in FIG. 4A. The wheels and gears can allow vessels to rotate and to be in contact with different heating plates. The vessels can be in the form of a cuvette, such as a capillary tube. They can be further disposed on a cassette or cassette pack, which can be further in contact with the heating plates; see FIG. 4B. The cassette can comprise depressions or grooves that are substantially of the same size and shape as the capillary tubes. The different components and views of the cassette, cassette holder, and an assembled cassette holder with cassette with capillary tubes are shown in FIGS. 5A-5C. The capillary tubes can carry the samples to be amplified and tested, and each capillary tube can fit into a groove on the cassette. The number of grooves, and hence the number of samples to be observed, can be of any number.

The thermocycler unit can be geared together to have one drive source. It can be indexed together to have substantially the same starting point. The design and material selection of the unit preferably is not susceptible to damages by chemicals used to sanitize before or after each test.

The temperatures of the center heating blocks, specifically those of the heating plates, and those around the periphery can be set by a user at any desirable temperature. For example, the temperature of the center heating blocks can be set at a first temperature, and half of the heating plates around the periphery can be set at a second temperature, with the remaining half being set at a third temperature. The first, second, and third temperatures can be the same or different from each other. For example, the second temperature can be the same as the third temperature, and both can be different from the first temperature to allow an isothermal amplification. Alternatively, all three temperatures can be different. In one embodiment, the heating plates of the central heating block have a temperature of between about 90° C. and about 100° C., such as about 95° C., the heating plates of three of the outside heating blocks have a temperature of about 50° C. to about 60° C., such as about 55° C., and those of three other outside heating blocks have a temperature of about 70° C. to about 75° C., such as about 72° C.

The thermocycler can be further automated and controlled by a microprocessor, such as a computer system with optionally suitable software. Commercial software such as Labview can be used.

In one embodiment, the thermocycler can provide at least 108 samples per hour to be tested in the field. In this embodiment, the entire test can be used without being connected to an external electrical outlet. As described before, the number of samples tested at once can be increased to 360 or higher per hour. Further, after each test is completed, the battery can be re-charged by the photovoltaic cells, and thus the thermocycler can be re-used repeatedly without changing the battery. Depending upon the design, the time to recharge the battery can vary. For instance, in one embodiment, the photovoltaic cells can charge the battery in, for example, about 12 hours or less, such as about 6 hours or less, such as 3 hours or less. Further, the thermocycler provides can provide readings of the test results with a fluorometer after each test on site.

Mechanical Aspect

Schematic of the mechanical aspect of the unit are shown in FIGS. 4A-4B. The unit can comprise built-in tooling for positioning the mechanism during assembly. Tooling pins can be used during assembly and/or installation of the mechanism. The mechanism can load the gears, preferably spider gears, towards the upper plate, as shown in FIG. 4A. A cassette holder can be mounted to reduce the gaps and need for high precision, high cost manufacturing. The mechanism can be designed with common parts to minimize part-count and to reduce costs.

The parts can be universal. For example, the parts can be isotropic, with substantially no need to be positioned upward, downward, rightward, or leftward. The design can allow a user to operate with minimal training and to reassemble if needed in the field. The bearing surfaces can also be geometrically maximized for stability. The pat inertia of the spider gears can be minimized for power demand.

Cassette

Cassette can have a dovetail bottom for each capillary tube to keep the tubes from falling through the cassette. At the bottom of the cassette, there can be disposed a bearing, which allows the cassette to be moved around the spider gears during movement. The sealed ends of the tubes can be visible at the top of the cassettes to provide the optical access necessary for fluorescent emissions or the like to be detected and the results communicated to the user.

To facilitate mounting of cassette on pegs or shafts, a three-pin sample wheel and a clip can be used. The cassette can be in a cassette holder, which can be a replaceable item by the removal of an e-clip, if the holder is damaged or worn out. Clip preferably has a resilient end that may be pinched together to allow the clip to be inserted into the cassette and then spring back once it reaches a circular space on the cassette. The clip also can have peg for coupling the clip to the peg.

The cassette holder can be used to hold a cassette. The holder can be manufactured by any methods such as injection molding. It can have face pressure springs designed in, and these springs can allow the cassette to contact the full fact of the heater block and provide for the variation of the position of the heater face. The design can also comprise a built-in spring float and a lateral float. The lateral float can allow the cassette to float into position when contacting the heater face, allowing alignment of the surface of the capillary tube and the surface of the heating plate. Schematics of cassette and cassette holders are shown in FIG. 5A-5C.

The cassette holder can have an opening in through the unit, such as one connecting the back and the front, to allow the cassette to be viewed during the thermocycling process. The cassette can have a similar window allowing the capillary tubes to be viewed from either the front of back during the operation. The cassette can be designed to hold any number of capillary tubes, and in one embodiment, the cassette can hold 6 capillary tubes. The capillary tubes can be supported from the rear on the cassette when in contact with the heating plate surface. The contact area of the two can be minimized to reduce thermal losses. The cassette can be further designed with a rear pocket for an RFID tag, which can carry data of the samples. The cassette can further have indexing points to locate the cassette in the cassette holder.

The cassette can further comprise a cap, as shown in FIG. 5C, to prevent the capillary tubes from slipping out of the cassette. The cap can have a tapered plug to sea the open end of the capillary tubes, and the cap can provide a snap fit to the cassette body. The bottom of the cassette can allow viewing of the sealed glass ends of the capillary tube for reading. The cassette can be designed to use minimal material, to be simple for mass production. Further, it can be designed to be reusable after each test, although a new cap may be used for a new test. Additionally, the cassette can assist in the snapping of the capillary tube stem after scoring.

In one embodiment, each capillary cassette is coupled to a clip, which can facilitate the coupling of the cassette to one of the pegs of one of the tri-pegged wheels. For example, in one embodiment, there are six groves on each of the six cassettes, and there are six center heating blocks, and twelve heating blocks around the periphery of the rotary plate. Thus, this embodiment can provide 108 samples to be observed on the rotary plate at one time. In another embodiment, in the center of the rotary plate, there can be also a fluorescence detection system. The system can comprise a fluorometer and a plurality of cables connected to the heating plates and the vessels. The fluorescence detection system can provide results after a user-defined number of cycles of amplification of the biomolecules in solution. The biomolecule can be any biomolecule, including polynucleotides, such as DNA, RNA, protein, peptides, or fragments thereof.

Heater

The faces of heating plates can comprise depressions, corresponding to the number, size, and/or shape of the vessels that are to be heated, thereby allowing a vessel to be heated on a greater surface area of the vessel. See FIG. 2. The heating plates can comprise holes, allowing cables, such as fiber optic cables, to pass through; see FIG. 2B. In one embodiment, each depression of the heating plate has two holes, allowing two cables to go through, with the cables attached to the heating plate. The cables can, for example, provide light and/or collect signals for the fluorescence detection system.

Figure 6:
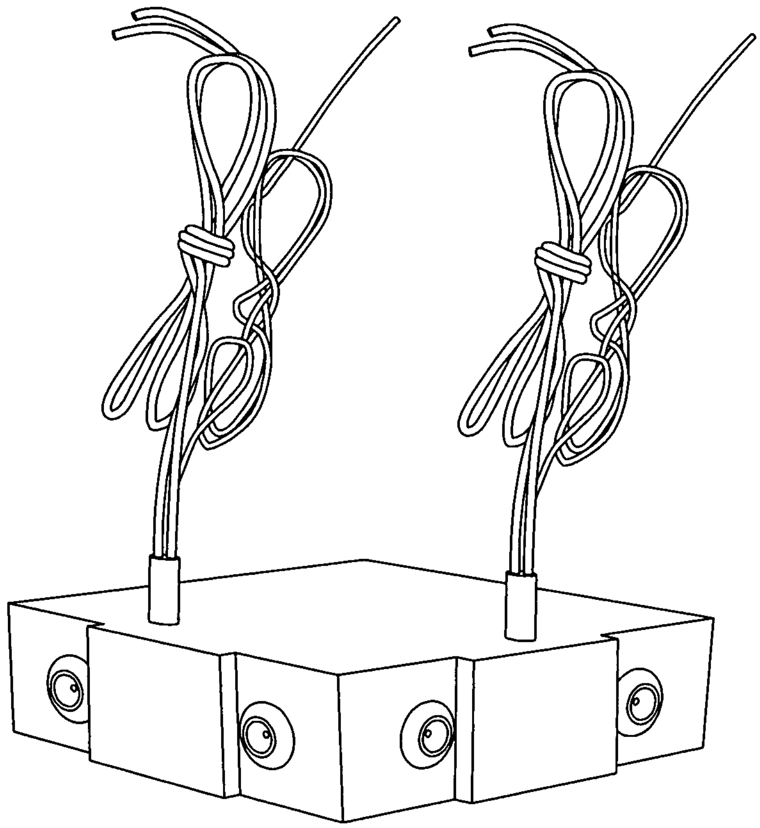
FIG. 6 provides an image of the heater.
Figure 7:
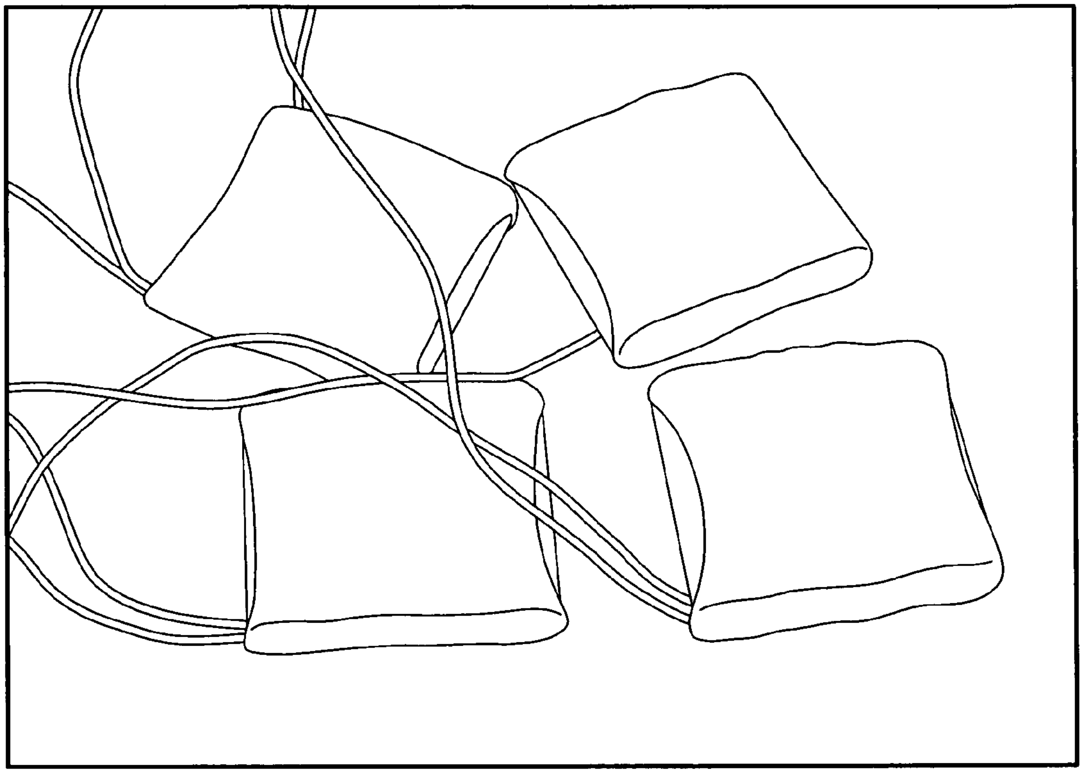
FIG. 7 provides an image of a series of lithium batteries as a power source in one embodiment.

The heating plates can communicate with a power source optionally via a microprocessor, such as a computer system. The power source can be a battery pack, such as one comprising 4 batteries, as shown in FIG. 7. In one embodiment, a heating element (also commonly referred to by a person skilled in the art as a Kapton heater, a Thermofoil heater, or a polyimide heating element) is used to raise the temperature of the heating plates. However, the heating element need not be restricted to a Kapton heater, a Thermofoil heater, or a polyimide heating element. Any heating element that has characteristics comparable to a Kapton heater, a Thermofoil heater, or a polyimide heating element can be used. In one embodiment, the heater or heating element is controlled by a low side N-channel MOSFET pass element, although the element need not be limited to this single implementation and could be implemented by way of a high side pass element, a single or plurality of operational power amplifiers, or by way of a software controlled pass, series, or parallel control element. FIG. 6 provides an image of a heater that can be used in one embodiment.

Each heating plate is connected to a heater. One desirable function for a field deployable thermocycler is the capability to reach a prescribed temperature within about 3 minutes. The design of a thin thermally conductive heating plate over a thicker thermally insulating heating block can help achieve this goal. Further, the temperature of each heating plate can be individually controlled to maximize rate of reaching the prescribed temperature and to minimize energy fluctuation and overall energy waste.

In one embodiment, a plurality of heaters are connected to all of the 18 heating plates, and the heaters are controlled by 18 individually tunable Proportional-integral-derivative (P-I-D) controller circuits, each having its own input and output.

PID can provide closed-loop control based on an error signal that is the difference between the desired set-point and the real time value of the process control variable, which is desired to reach and maintain, as quickly and without oscillation above and below the prescribed value as possible, respectively. The prescribed value can be set by a user via a computer software control system. For example, a user can input desired values for a set of temperatures with a keyboard into a computer, and a software can then implement these values and transmit instructions to the PID heaters. For each heater element there can be three circuit sections that individually address the proportional (linear or "proportionally" scaled difference "error" value between the desired set-point value and real time measured value); the Integral (the sum history of recent "error" values between desired set-point value and real time measured value); and the Derivative (rate of change of the "error" value between the desired set-point value and the real time measured value) terms of the controller.

PID that can be used need not be restricted to individually tunable amplifiers. All methods based on PID implementation can be employed, including software/firmware PID control, single operational amplifier configuration PID control, or a combination thereof. PID may also be accomplished by way of a single operational amplifier section containing all three terms or by way of software control. In one embodiment, three terms are linearly added by way of an individual operational summing amplifier, with user adjustable potentiometer control for the "weight" of each of the PID terms. This can also be accomplished in other methods or means such as resistive divider or software controlled "weighting" of each of the terms.

In the implementation described herein, the summation of the individually weighted PID terms are delivered to a final gain stage on an operational amplifier, which is also performing the summation of the PID terms. Alternatively, an amplifier composed of a single or multiple number of transistors, or by software control of a analog-to-digital converter may also be used.

A temperature measuring device can be used to detect and measure temperature of the heating plate, which can transfer heat to the samples within the capillary tubes. The temperature measuring device can be a temperature measuring transducer, such as a thermocouple. In one embodiment, a Resistive Thermal Device (RTD) can be used. A constant current source can be used to excite the RTD in a multi-wire configuration to maintain the highest level of accuracy. The multi-wire configuration can comprise any number of wires, such as two, three or four wires.

The RTD features a variable resistance which can vary linearly with temperature. In one embodiment, an instrumentation amplifier can comprise three operational amplifier sections to amplify the voltage developed across the RTD. Alternatively, amplification can be accomplished by way of, for example, a monolithic instrumentation amplifier IC or any other method of amplification, such as discrete transistor implementations.

In one embodiment, a set-point control circuit can be implemented by way of a precision voltage band-gap reference and an operational amplifier with user adjustment potentiometer. Alternatively, set-point control can be accomplished by other methods, including a simple resistor voltage divider or output from a software controlled Analog to Digital (A/D) converter.

Additionally, in one embodiment, a summing amplifier based upon a single operational amplifier is disclosed to "add" together a positive set-point value and a negative measured value is deployed to derive the "error signal." Other implementations can also be used, including adding a negative set-point value and positive measured value by an operational summing amplifier; or software means of quantification of error values by way of analog to digital conversion of set-point and measured values for mathematical.

Motor and Gears

Disposed on the rotary can be a plurality of rotating wheels fixed to cooperating meshed gears. The wheels can be tri-pegged wheels, and the gears can be, for example, spider gears. The meshed spider gears can be used to power and move the rotary plate. Each gear can include a spindle, which travels through, but does not generally drive wobble gears. Interlocking meshed gears may also be moved by applying a force to any one of the gears. Accordingly, a motor may be provided for powering the rotary plate, while maintaining the light, portable, and efficient nature of the device.

Various motors can be used. In one exemplary embodiment, a bipolar stepper motor is deployed to engage the spider gears which operate the positioning of each cassette during the thermal cycling process. Alternatively, other motors, such as a unipolar stepper motor, a DC brush servo motor, a DC brushless servo motor, or any other electrical motor which converts electrical energy into mechanical force and/or angular displacement, can be used. The motor and its driver can be controlled by a microprocessor, such as a computer, allowing user-defined commands, including, for example, the number of cycles. A schematic of a circuit diagram of the motor and the driver, as well as the encoder, is provided in FIG. 8.

An encoder, such as an optical encoder, can be used to calculate and identify the position of a stepper motor. Alternatively, calculation and identification of the motor position may be accomplished by any method of counting the stepper motor drive steps, including an optical or mechanical limit switch, or any other transducer that could identify position of the cassettes during the thermal cycling process.

In one embodiment, a semiconductor-based Full "H-Bridge" drive circuit is deployed. The circuit comprises two Full Bridge Pulse Width Modulation (PWM) Micro-stepper motor drivers which are utilized to drive the motor. Alternatively, other implementations to drive the motors can be used, including a semiconductor based half bridge drive; mechanical relays, switches or other drive methods.

The number of wheels and gears can vary according to the design of the thermocycler. For example, in one embodiment, six-rotating tri-pegged wheels are used. Of this embodiment, each tri-pegged wheel is capable of accepting three cassettes, thereby forming a cassette cluster. This configuration can allow for 18 capillary tubes (in 3 cassettes of 6 tubes) to be loaded on each of the 6 tri-pegged wheels (3 cassettes per wheel), allowing each of the 108 faces of the hexagonal arrangement of heating faces of the device to be in contact with a capillary cassette. Accordingly, 108 capillary tubes or reaction vessels can be processed at one time and no excess heat is wasted because each face is engaged at all relevant times. Accordingly, with this configuration, the 120 degree rotation from one block to another can be performed. Each rotating sample wheel can rotate in a direction opposite to adjacent wheels. For example, the 95° C. block is shared by all six cassette clusters, while the 55° C. and 72° C. blocks are shared by adjacent sample clusters.

It is noted that the number of capillary tubes on the cassettes and the number of cassettes can be varied, as described previously. In addition, any number of tubes may be treated at one time, and any suitable geometrical configuration of heat blocks may be used according to the design described herein. For example, in an alternative embodiment, up to 360 samples can be processed at one time.

Fluorometer

DNA detection systems commonly use FIFO (first in first out) methods when delivering results for tests that are being processed on-board. This is because most DNA diagnostic instruments are batch analyzers and all tests with the same protocol must be run together. Therefore, tests should be placed in the processing queue in the order of the desired output sequence.

The detection systems can overcome these shortcomings by, for example, having a fluorometer designed to read DNA in a capillary tube that is positioned in front of it by spider gears moving a small rotating carousel. In one embodiment, there are six sets of spider gears and six rotating carousels. The spider gears position the capillary tubes in front of six heating plates located in an inner circle in the center of the device. Amplification of the DNA can take place by rotating the capillary tubes from one temperature heating plate to the next. The capillary tubes can be positioned in front of the heating plates, which have depressions matching the size and configuration of the tubes to hold them in a stable position while the reading takes place. The heating plates can have two small holes in each slot to permit 1 mm fiber optic cables to attach to each hole so as to form a small tunnel for light to pass through.

Figure 9:
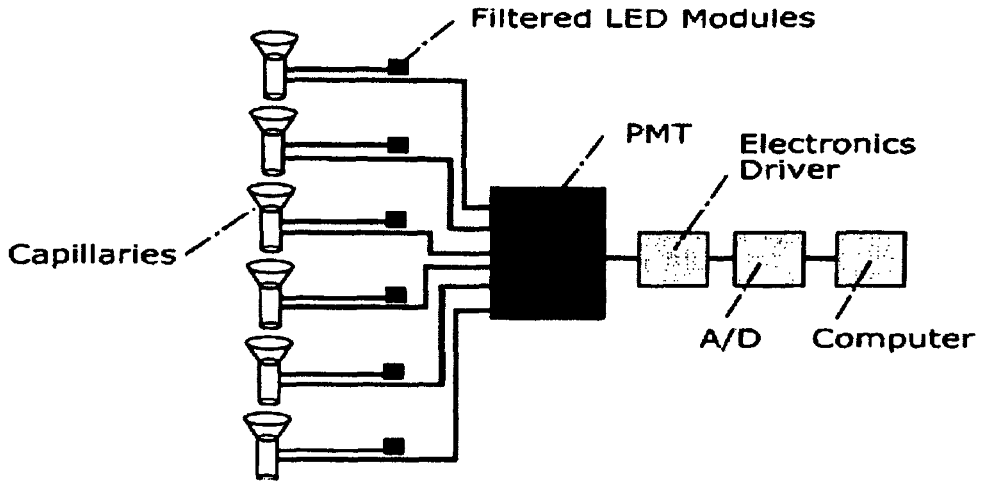
FIG. 9 illustrates a schematic of the design of the fluorescence detection system.

Various designs of the cables can be used. For example, one single cable can be used to emit and collect fluorescence. Preferably, two cables are used per one capillary tube, with one cable used for emission and/or excitation, and the other for collection. See FIG. 9. The latter design can provide fewer errors and more efficient detection of responses. The low level of errors is particularly desirable in a clinical setting. This design can be also adapted to perform other detection modalities, including molecular beacon multiplexing.

A light source can be emitted through the fiber optic cables by LED stationed in a light box. The fiber optic cables can enable maximum coupling of the LED light into the excitation fiber of the fiber optic cable. The cable can deliver the excitation light from the light source to the test object sample capillary tube. The emission from the fiber optic cable located below the excitation fiber optic cable can be coupled to the capillary test object and collects the fluorescence from the capillary tube, which have been excited by the light coming through the excitation fiber optic cables, and delivers it to the detection unit fiber coupler. The collected fluorescence enters the detection unit from the collection fibers to the fiber optic coupling block, which collimates the divergent light exiting from the end of the collection fiber.

The fluorescence light can enter a photo multiplier tube (PMT) or a photodiode optic block. The detection light can be further filtered prior to detection with interference filters placed in the PMT block. A photodiode can allow detection of reflected light. The PMT can be powered by an electronic driver and can be further coupled to a analog-to-digital (A/D) converter. The A/D converter can be controlled by a microprocessor, such as the BitsyXβ single board computer. See the schematic as provided in FIG. 9.

In one embodiment, the fiber optic cables permit light to pass through the top hole and illuminate the capillary tubes containing aqueous solution. The bottom hole has a 1 mm fiber optic cable attached to it to permit light from the illuminated solution to be collected and pass back to the PMT. The PMT (photomultiplier tube) detects the light emitted from the capillary tube and amplifies it. The electronics driver is interfaced to the PMT and controls the gain experienced by the PMT while collecting the emitted light. The A/D converts the low level analog signal to a digital output for data reduction by the BitsyXβ single board computer.

In another embodiment, the capillary tubes are cycled through the various temperature heating plates for about 20 cycles. The number of cycles can vary, depending on the user input. After the last cycle, the first group of 36 capillary tubes are rotated in front of the fiber optic cables connected to the fluorometer to be read. They may be read in any order desired by the user. After the first 36 are read, the second group of 36 is rotated in front of the fiber optic cables connected to the fluorometer for reading, and the groups may be read in any order, thereafter the last group of 36 is rotated in front of the fiber optic cables connected to the fluorometer for reading; the groups may be read in any order.

Case

Figure 10A:
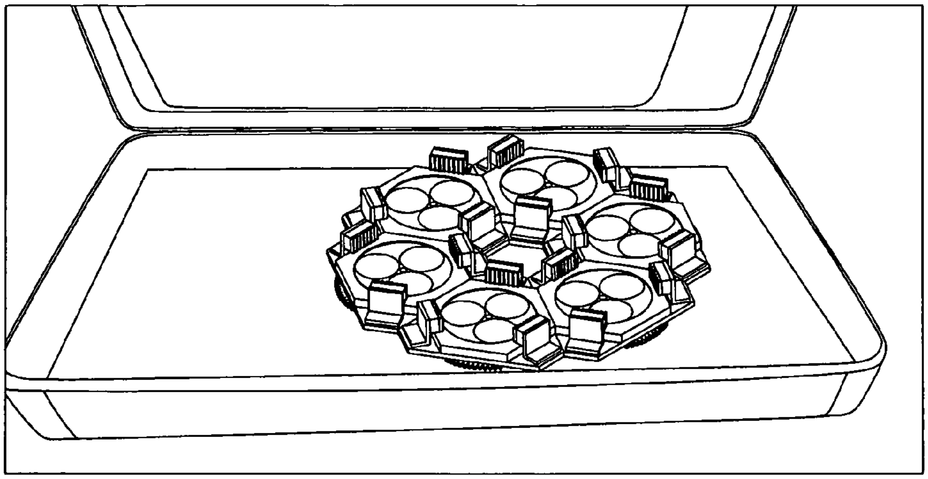
FIGS. 10A-10C provide illustrations of the portable thermocycler device.

The case can further provide additional functionalities to the thermocycler operation. The case that houses the thermocycler described herein can be of any size, but preferably it is of a suitable size and weight to maintain the device's portability. It is preferably similar to the dimensions of a laptop computer. See e.g., FIG. 10A. For example, its width can be less than about 35 inches, such as less than about 20 inches, such as less than about 15 inches; its length can be less than about 30 inches, such as less than about 20 inches, such as less than about 10 inches; its thickness can be less than about 15 inches, such as less than about 10 inches, such as less than about 5 inches. In one embodiment, the case is about 17 inches wide, about 15 inches long, and about 7 inches thick. The weight of the case can also vary, depending on the design. For example, it can be about 35 lbs or less, such as about 20 lbs or less such as about 12 lbs.

Figure 10B:
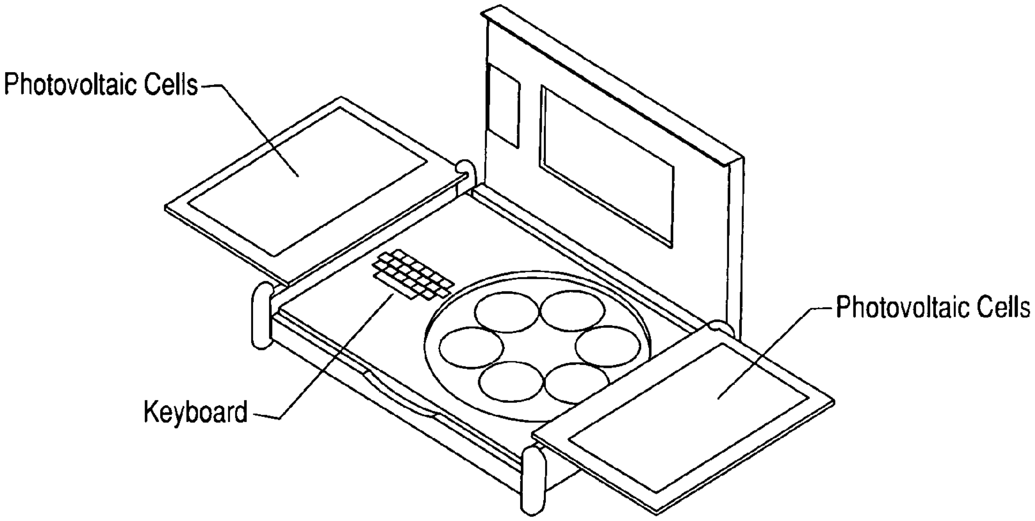

The case can comprise a keyboard, allowing the user to interface and control the thermocycler via a microprocessor such as a computer. The keyboard can be located on any suitable space in the case. See e.g., FIG. 10B. The keyboard can be of any type of keyboard. For example, it can be one used for conventional desktop or laptop computers, soft or hard touchpads, or virtual keyboard utlizing laser. A virtual keyboard can have an advantage of lighter weight and avoiding possible fluid spill on the keyboard. The case can further comprise a display, such as a digital display, such as a LED display. The display can be of any suitable size and configuration. The display can provide an interface for the user to input commands, monitor testing conditions, and/or obtain results from, for example, the fluorescence reading after a test is completed.

The LED information may be provided by any suitable manner. The detector preferably detects the presence or lack of presence of a marker's fluorescent emission after completion of a PCR procedure.

The case also houses the power source for the device, such as a battery pack. In most embodiments, the thermocycler is powered by at least one battery, for example one, two, three, four or more batteries. The voltage of each battery need not be restricted to a certain value. The number and type of battery depends on the use of the thermocycler. The battery can be rechargeable battery. For example, it can comprise nickel, such as nickel metal hydride and nickel cadmium, or it can comprise lithium, such as lithium ion or lithium polymer. See e.g., FIG. 7. The case can further comprise at least one photovoltaic cell and/or solar cell. See e.g., FIG. 10B. Photovoltaic and solar cells are generally known in the art. In one embodiment, the case comprises two photovoltaic cells. The photovoltaic cells can recharge the rechargeable batteries so that the device may be used in the field without a need to recharge via an electrical outlet and/or to replace the batteries after each test.

Figure 10C:
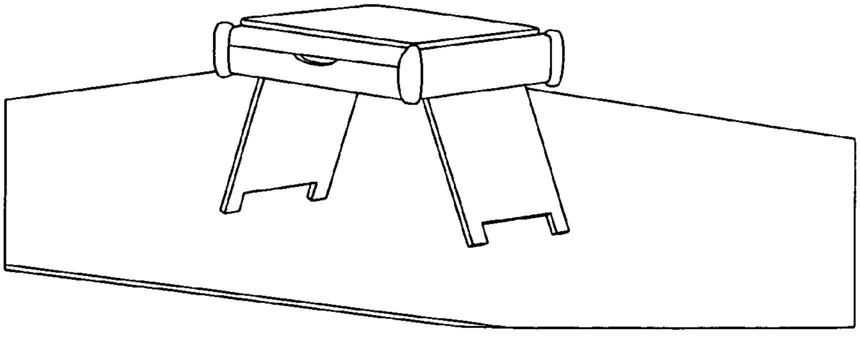

The case may comprise components that resemble foldable legs. In one embodiment, the two pieces at the bottom of the case can be unfolded and provide vertical support for the case. See e.g., FIG. 10C. The fully extended legs can be of any desirable height. For example, it can be 1 foot, or it can be 2 ft or more.

Non-Limiting Working Example

Method

Sample preparation and analysis are integrated in a self-contained capillary tube using "Hot Start Polymerase." The capillary tube is manufactured with probes and reagents specific to each assay.

Process A.

Sample is placed in the funnel which contains buffers and Pgem extraction enzyme (see FIG. 11A).

Step 1A: The capillary tubes are rotated to the 75° C. heater block and held for 15 minutes to extract DNA from sample.

Step 2A: The capillary tubes are then rotated to the 95° C. heater block where the enzyme is inactivated. At the same time the wax plug is melted releasing the polymerase and initiating the reaction ("Hot Start Polymerase").

Step 3A: The total solution flows into the lower capillary tube where it is cycled through all three temperatures—55° C., 75° C., and 95° C.—for 20 cycles to amplify the DNA.

Process B

Step 1B: After the last cycle, each capillary is rotated to the read station located in the center section of processing station and each capillary tube is read by the fluorometer individually in sequence.

Results

Specific and sensitive analysis using nucleic acid amplification protocols are prepared and performed using completely self contained packaging, minimizing the potential of contamination and allowing high throughput in a variety of environments. The fluorescence results are shown FIG. 11B.

The examples provided are for illustrative purposes only and should not be construed as limiting the scope of the invention. Other embodiments of the invention are readily apparent to those of ordinary skill in the art in view of the disclosure and teachings provided in this specification.

What is claimed:

1. A portable thermocycler comprising a case;

a rotary plate in the case;

a plurality of heating blocks arranged in a geometric pattern disposed on the rotary plate; and at least one vessel adapted to move and contact at least two of the plurality of heating blocks;

wherein each of the plurality of heating blocks comprises a heating element having opposing sides, one side contacting a heating plate and an opposing side contacting a thermally insulating material, such that each of the plurality of heating blocks is individually and independently maintained at a desired temperature;

wherein the geometric pattern comprises a plurality of center heating blocks arranged in a shape defining a polygon and a plurality of outside heating blocks disposed around a periphery of the rotary plate; and wherein the rotary plate includes a plurality of rotating wheels adapted to rotate at least one of the vessels into contact with at least one of the plurality of center heating blocks and at least one of the plurality of outside heating blocks.

2. The thermocycler of claim 1, wherein the heating plate comprises a material with higher thermal conductivity than that of the thermally insulating material.

3. The thermocycler of claim 1, wherein the thermally insulating material comprises a thermoplastic.

4. The thermocycler of claim 1, wherein the heating plate comprises aluminum.

5. The thermocycler of claim 1, wherein the heating plates of the center heating blocks have a first temperature, half of the number of the outside heating blocks have a second temperature, and the other half of the number of outside blocks have a third temperature; wherein the third temperature is intermediate between the first and the second temperatures.

6. The thermocycler of claim 1, wherein the heating plates of the central heating block have a temperature of between about 90° C. and about 95° C., the heating plates of half of the outside heating blocks have a temperature of about 50° C. to about 60° C., and the remaining half of the outside heating blocks have a temperature of about 70° C. to about 75° C.

7. The thermocycler of claim 1, further comprising at least one Proportional Integral Derivative (PID) controlling circuit for each heating element.

8. The thermocycler of claim 1, further comprising a Resistive Thermal Device adapted to measure the temperature of the heating plate.

9. The thermocycler of claim 1, wherein the rotating wheels are adapted to rotate a plurality of vessels into contact with at least one of the plurality of center heating blocks and at least one of the plurality of outside heating blocks.

10. The thermocycler of claim 1, wherein the number of the outside heating blocks is at least the same as the number of the center heating blocks.

11. The thermocycler of claim 1, the rotating wheels further comprise tri-pegged wheels maneuvered by spider gears.

12. The thermocycler of claim 1, wherein the case comprises at least one photovoltaic cell.

13. The thermocycler of claim 1, wherein the case comprises at least one keyboard.

14. The thermocycler of claim 1, wherein the case comprises at least one display.

15. The thermocycler of claim 1, wherein the case comprises foldable legs.

16. The thermocycler of claim 1, further comprising a fluorescence detection system.

17. The thermocycler of claim 16, wherein the fluorescence detection system further comprises a plurality of sets of two cables, wherein one of the cable in the set is adapted to excite fluorescence and the other is adapted to collect fluorescence.

18. The thermocycler of claim 1, wherein the thermocycler is powered by at least one battery.

19. The thermocycler of claim 1, wherein the thermocycler is controlled by a microprocesser.

20. A portable thermocycler comprising:

a case;

a rotary plate in the case;

a plurality of heating blocks arranged in a geometric pattern disposed on the rotary plate; and at least one vessel adapted to move and contact at least two of the plurality of heating blocks;

wherein at least some of the plurality of heating blocks comprise a heating element having opposing sides, one side contacting a heating plate and an opposing side contacting a thermally insulating material having a thickness greater than that of the heating plate;

wherein each heating element is individually controlled by a proportional-integral-derivative (PID) controlling circuit;

wherein the thermocycler is powered by at least one battery; and wherein the rotary plate includes a plurality of rotating wheels adapted to rotate at least one of the vessels into contact with at least one of the plurality of center heating blocks and at least one of the plurality of outside heating blocks.

21. The portable thermocycler of claim 20, wherein the heating blocks are arranged in a geometric pattern comprising a number of center heating blocks arranged in a shape defining a polygon and a number of outside heating blocks disposed around a periphery of the rotary plate.

22. The thermocycler of claim 20, wherein the heating plate comprises a material with higher thermal conductivity than that of the thermally insulating material.

23. The thermocycler of claim 20, wherein the heating plate comprises aluminum.

24. The thermocycler of claim 20, further comprising individually tunable operational amplifier sections, software or firmware PID control, single operational amplifier configuration PID control that are capable of controlling the heating element, or a combination thereof.

25. The thermocycler of claim 20, wherein the plurality of rotating wheels are maneuvered by spider gears having spindles associated with the wheels.

26. The thermocycler of claim 20, further comprising a temperature measuring transducer adapted to measure the temperature of the heating plate.

27. The thermocycler of claim 20, further comprising a thermocouple adapted to measure the temperature of the heating plate.

28. The thermocycler of claim 20, further comprising a Resistive Thermal Device (RTD) adapted to measure the temperature of the heating plate.

29. The thermocycler of claim 20, further comprising a fluorescence detection system.

30. The thermocycler of claim 20, wherein the case comprises at least one photovoltaic cell.

31. A portable thermocycler comprising:

a case;

a rotary plate in the case;

a plurality of heating blocks arranged in a geometric pattern disposed on the rotary plate; and at least one vessel adapted to move and contact at least two of the plurality of heating blocks;

wherein each of the plurality of heating blocks comprises a heating element having opposing sides, one side contacting a heating plate and an opposing side contacting a thermally insulating material having a thickness greater than that of the heating plate;

wherein the thermocycler is powered by at least one battery;

wherein the case comprises at least one photovoltaic cell; and wherein the rotary plate includes a plurality of rotating wheels adapted to rotate at least one of the vessels into contact with at least one of the plurality of center heating blocks and at least one of the plurality of outside heating blocks.

32. The thermocycler of claim 31, wherein the battery is a rechargeable battery.

33. The thermocycler of claim 31, wherein the heating plates of the central heating block have a first temperature, and the outside blocks have a second temperature, wherein the first and second temperature are substantially the same or different.

34. The thermocycler of claim 31, wherein the case comprises a display, a keyboard, or a combination thereof.

35. A portable thermocycler comprising:

a case;

a rotary plate in the case;

a plurality of heating blocks arranged in a geometric pattern disposed on the rotary plate;

at least one vessel adapted to move and contact at least two of the plurality of heating blocks; and a fluorescence detection system;

wherein each of the plurality of heating blocks comprises a heating element having opposing sides, one side contacting a heating plate and an opposing side contacting a thermally insulating material having a thickness greater than that of the heating plate; and wherein the rotary plate includes a plurality of rotating wheels adapted to rotate at least one of the vessels into contact with at least one of the plurality of center heating blocks and at least one of the plurality of outside heating blocks.

36. The portable thermocycler of claim 35, wherein the fluorescence detection system comprises a plurality of sets of two cables, wherein one of the cables in the set is adapted to excite fluorescence and the other is adapted to collect fluorescence.

37. The portable thermocycler of claim 35, wherein the fluorescence detection system comprises a photomultiplier tube or a photodiode.

38. The portable thermocycler of claim 35, wherein the fluorescence detection system comprises an analog-to-digital converter.

39. The portable thermocycler of claim 35, wherein the fluorescence detection system is controlled by a microprocessor.

40. The portable thermocycler of claim 35, wherein the vessel carries a plurality of capillary tubes.

* * * * *